US005929245A

United States Patent [19]

Grund et al.

[11] Patent Number: 5,929,245

[45] Date of Patent: Jul. 27, 1999

[54] NAPHTHOLACTAM DYES

[75] Inventors: Clemens Grund, Mannheim; Ernst Schefczik, Ludwigshafen; Gunther Lamm, Hassloch; Roland Merger, Bad Schönborn; Rüdiger Sens, Mannheim, all of Germany

[73] Assignee: BASF Aktiengesellschaft, Ludwigshafen, Germany

[21] Appl. No.: 08/776,596

[22] PCT Filed: Aug. 4, 1995

[86] PCT No.: PCT/EP95/03112

§ 371 Date: Feb. 18, 1997

§ 102(e) Date: Feb. 18, 1997

[87] PCT Pub. No.: WO96/06137

PCT Pub. Date: Feb. 29, 1996

[30] Foreign Application Priority Data

Aug. 19, 1994 [DE] Germany ............................ 44 29 548

[51] Int. Cl.$^6$ ...................... C07D 401/04; C07D 495/04; C09B 57/06

[52] U.S. Cl. ........................................ 546/276.7; 546/288

[58] Field of Search .......................................... 546/276.7

[56] References Cited

FOREIGN PATENT DOCUMENTS

| | | |
|---|---|---|
| 0 416 434 A3 | 7/1992 | European Pat. Off. . |
| A 2 344 603 | 10/1977 | France . |
| A 20 25 427 | 9/1971 | Germany . |
| 2611665 C2 | 6/1978 | Germany . |
| A 27 05 108 | 10/1978 | Germany . |

OTHER PUBLICATIONS

Chemical Abstracts, vol. 99, No. 4, Jul. 25, 1983, Columbus, Ohio, US, Abstract No. 24028K.

Chemical Abstracts,vol. 87,No.26,abst.203,077z pub.Dec. 16,1977.

Chem.Abstracts,vol.89,No.22,Abst.No.181223,abstracting German Offen.[DE]2705108, pub.Aug. 10, 1978.

*Primary Examiner*—Alan L. Rotman

*Attorney, Agent, or Firm*—Oblon, Spivak, McClelland, Maier & Neustadt, P.C.

[57] ABSTRACT

(I)

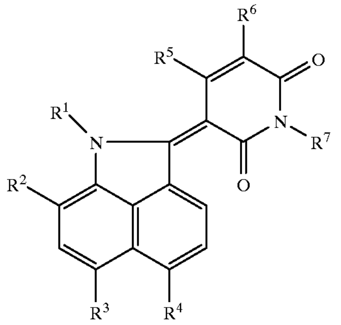

(II)

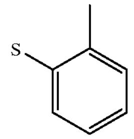

The invention concerns naphtholactam derivatives of formula (I), in which: $R^1$ represents hydrogen, optionally substituted $C_1$–$C_6$ alkyl $C_5$–$C_6$ cycloalkcyl or substituted phenyl; $R^2$ and $R^3$ represent hydrogen, $C_1$–$C_8$ alkanoyl, optionally substituted benzoyl, optionally substituted $C_2$–$C_4$ alkyl, optionally substituted $C_2$–$C_4$ alkenyl, optionally substituted $C_2$–$C_4$ alkinyl, a halogen, nitro, sulphamoyl, optionally substituted hydroxy, optionally substituted mercapto, $C_1$–$C_6$ alkysulphonyl or optionally substituted phenylsulphonyl; $R^4$ represents hydrogen or, with $R^3$, a group of formula (II); $R^5$ represents hydrogen or $C_1$–$C_6$ alkyl; $R^6$ represents cyano, carbamoyl, $C_1$–$C_4$ mono- or dialkylcarbamoyl carboxyl or $C_1$–$C_4$ alkoxycarbonyl; and $R^7$ represents substituted $C_1$–$C_4$ alkyl, optionally substituted $C_5$–$C_{13}$ alkyl or benzoyl. Also disclosed is the use of these derivatives for dyeing or printing textiles.

11 Claims, No Drawings

NAPHTHOLACTAM DYES

CROSS REFERENCE

This application is a 371 of PCT/UEP 95/03112 filed Aug. 4, 1995.

The present invention relates to novel naphtholactam derivatives of the formula I (I)

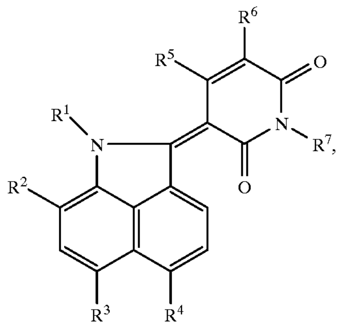

where $R^1$ is hydrogen, substituted or unsubstituted $C_1$–$C_6$-alkyl, $C_5$–$C_7$-cycloalkyl or substituted or unsubstituted phenyl, R2 and $R^3$ are independently of each other hydrogen, $C_1$–$C_8$-alkanoyl, substituted or unsubstituted benzoyl, substituted or unsubstituted $C_2$–$C_4$-alkyl, substituted or unsubstituted $C_2$–C4-alkenyl, substituted or unsubstituted $C_2$–$C_4$-alkynyl, nitro, sulf amoyl hydroxyl, mercapto, $C_1$–$C_6$-alkoxy, substituted or unsubstituted phenoxy, $C_1$–$C_6$-alkylthio, substituted or unsubstituted phanylthio, $C_1$–$C_6$-alkylsulfonyl or substituted or unsubstituted phenylsulfonyl, $R^4$ is hydrogen or together with $R^3$ a radical of the formula

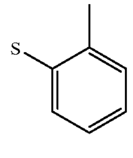

, $R^5$ is hydrogen, $R^6$ is cyano, carbamoyl, mono- or di($C_1$–$C_4$-alkyl) carbamoyl, carboxyl or $C_1$–$C_4$-alkoxycarbonyl, and $R^7$ is substituted or unsubstituted $C_5$–$C_{13}$-alkyl with or without interruption by from 1 to 3 oxygen atoms in ether function, by from 1 to 3 sulfur atoms or by from 1 to 3 imino or $C_1$–$C_4$-alkylimino groups, or is benzoyl, and to their use for dyeing or printing textile materials.

DE-A-2 611 6685 (≈FR-A-2 344 603) and U.S. Pat. No. 4,096,145 disclose dyes based on similar naphtholactam derivatives. However, it has been found that the products described therein have application defects.

DE-A-2 705 108 and Chem. Abstr. 99 1983, 24028k, also describe naphtholactam dyes.

It is an object of the present invention to provide novel naphtholactam dyes which show advantageous application properties. More particularly, the novel dyes shall possess high color strength and brilliance and have good in-use/service properties.

We have found that this object is achieved by the above-defined naphtholactam derivatives of the formula I.

Any alkyl or alkenyl appearing in the abovementioned formulae may be straight-chain or branched.

Any substituted alkyl appearing in the abovementioned formulae may have as substituents for example cyclohexyl, phenyl, $C_1$–$C_4$-alkylphenyl, $C_1$–$C_4$-alkoxyphenyl, halophenyle $C_1$–$C_{13}$-alkanoyloxy, $C_1$–$C_{13}$-alkoxycarbonyl, $C_1$–$C_{13}$-alkoxycarbonyloxy, the alkyl chain of the three all [sic] last-mentioned radicals being optionally interrupted by from 1 to 3 oxygen atoms in ether function and/or phenyl- or phenoxy-substituted, cyclohexyloxy, phenoxy, halogen, hydroxyl or cyano. The number of substituents in substituted alkyl is generally 1 or 2.

Any interrupted alkyl appearing in the abovementioned formulae is preferably interrupted, unless otherwise stated, by 1 or 2 oxygen atoms in ether function, sulfur atoms or imino or $C_1$–$C_4$-alkylimino groups.

Any substituted phenyl appearing in the abovementioned formulae may have as substituents for example, unless otherwise stated, $C_1$–$C_8$-alkyl, $C_1$–$C_8$-alkoxy, nitro or halogen, especially chlorine or bromine. The number of substituents in substituted phenyl is generally from 1 to 3.

Any substituted alkenyl appearing in the abovementioned formula I may have as substituents for example phenyl, $C_1$–$C_{13}$-alkoxy-carbonyla cyano or hydroxyl. The number of substituents in substituted alkenyl is generally one.

Any substituted alkynyl appearing in the abovementioned formula I may have as substituents for example hydroxyl, phenyl, $C_1$–$C_{13}$-alkoxycarbonyl or cyano. The number of substituents in substituted alkynyl is generally one.

$R^1$ and $R^5$ are each for example methyl or else—and this also applies to $R^2$ and $R^3$ —ethyl, propyl, isopropyl, butyl, isobutyl, sec-butyl or tert-butyl.

$R^1$ and $R^5$ may each also be for example—and this also applies to $R^7$ —pentyl, isopentyl, neopentyl, tert-pentyl, hexyl or 2-methylpentyl.

$R^7$ may also be for example heptyle 1-ethylpentyl, octyl, 2-ethylhexyl, isooctyl, nonyl, isononyl, decyl, isodecyl, undecyl, dodecyl, tridecyl, isotridecyl (the above designations isooctyl, isononyl, isodecyl and isotridecyl are trivial names derived from the oxo process alcohols—cf. Ullann's Encyclopedia of Industrial Chemistry, 5th Edition, Vol, A1, pages 290 to 293, and also Vol. A 10, pages 284 and 285), 2-propoxyethyl, 2-isopropoxyethyl, 2-butoxyethyl, 2- or 3-ethoxypropyl, 2- or 3-propoxypropyl, 2- or 3-butoxypropyl, 2- or 4-methoxybutyl, 2- or 4-thoxybutyl, 2- or 4propoxybutyl, 3,6-dioxaheptyl, 3,6-dioxaoctyl, 4,8-dioxanonyl, 3,7-dioxaoctyl, 3,7dioxanonyl, 4,7dioxaoctyl, 4,7-dioxanonyl, 2- or 4-butoxybutyl, 4,8-dioxadecyl, 3,6,9-trioxadecyl, 3,6,9-trioxaundecyl, 3,6,9-trioxadodecyl, 4,11-dioxapentadecyl, 6-phenoxy-4-oxahexyl, 3-phenoxy-4-oxahexyl, 2- or 3-ethylthiopropyl, 2- or 4-methyithiobutyl, 2- or 4-ethylthiobutyl, 2-dimethylaminopropyl, 4-aza-4-methylpentyl, 2-ethylaminopropyl, 4-azahexyl, 2-diethylaminopropyl, 4-aza-4-ethylhexyl, 5-azahexyl, 5-aza-5-methylhexyl, 5-azaheptyl, 5-aza-5-ethylheptyl, 3,6-diazaheptyl, 3,6-diaza-6-methylheptyl or 3,6-diaza-3,6-dimethylheptyl.

$R^1$, R2 and $R^3$ may each also be 2-methoxycarbonylethyl, 2-ethoxycarbonylethyl, 2- or 3-methoxycarbonylpropyl, 2- or 3-ethoxycarbonylpropyl, 2- or 3-butoxycarbonylpropyl, 4-methoxycarbonylbutyl, 4-ethoxycarbonylbutyl, 2-methoxycarbonyloxyethyl, 2-ethoxycarbonyloxyethyl, 2- or 3-methoxycarbonyloxypropyl, 2- or 3-ethoxycarbonyloxypropyl, 2- or 4-methoxycarbonyloxybutyl, 2- or 4-ethoxycarbonyloxybutyl, 2-cyanoethyl, 2- or 3-cyanopropyl, 4-cyanobutyl, 2-acetyloxyethyl, 2-propionyloxyethyl, 2- or 3-acetyloxypropyl, 2-hydroxyethyl, 2- or 3-hydroxypropyl, 4-hydroxybutyl, 2-cyclohexyloxyethyl, 2- or 3-cyclohexyloxypropyl, 2- or 4-cyclohexyloxybutyl, phenoxymethyl, 2-phenoxyethyl, 2- or 3-phenoxypropyl, 2- or 4-phenoxybutyl, 2-cyclohexylethyl, 2- or 3-cyclohexylpropyl or benzyl, 1- or 2-phenylethyl, 2-chloroethyl, 2- or 3-chloropropyl or 2- or 4-chlorobutyl.

$R^1$ may also be for example cyclopentyl, cyclohexyl, cycloheptyl, phenyl, 2-, 3- or 4methylphenyl, 2,4-dimethylphenyl, 2-, 3- or 4-methoxyphenyl, 2,4-dimethoxyphenyl, 2-, 3- or 4-chlorophenyl or 2,6-dichlorophenyl.

$R^2$ and $R^3$ may each also be for example formyl, acetyl, propionyl, butyryl, isobutyryl, pentanoyl, isopentanoyl, hexanoyl, heptanoyl, octanoyl, 2-ethylhexanoyl, benzoyl, 2-, 3- or 4-methylbenzoyl, 2-, 3- or 4-methoxybenzoyl, 2-, 3- or 4-chlorobenzoyl, allyl, methallyl, styryl, 2-methoxycarbonylprop-1-en-1-yl, 2-ethoxycarbonylpropl1-en-1-yl, 2-(2-ethylhexyloxycarbonyl) prop-1-en-1-yl, 2-tridecyloxycarbonylprop1-en-1-yl, 2-isotridecyloxycarbonylprop-1-en-1-yl, ethynyl, prop-1-yn-1-yl, prop-1-yn-3-yl, 3-hydroxyprop-1-yn-1-yl, but-1-yn-1-yl, but-2-yn-1-yl, methylthio, ethylthio, propylthio, isopropylthio, butylthio, isobutylthio, pentylthio, hexylthio, phenylthio, 2-methylphenylthio, 2-methoxyphenylthio, 2-chlorophenylthio, methoxy, ethoxy, propoxy, isopropoxy, butoxy, isobutoxy, sec-butoxy, pentyloxy, isopentyloxy, neopentyloxy, tert-entyloxy, hexyloxy, 2-methylpentyloxy, phenoxy, 2-, 3- or 4-methylphenoxy, 2-, 3- or 4-methoxyphenoxy, methylsulfonyl, ethylsulfonyl, propylsulfonyl, isopropylsulgonyl, butylsulfonyl, isobutylsulfonyl sec-butylsulfonyl, pentylsulfonyl, isopentylsulfonyl, neopentylsulfonyl, hexylsulfonyl, phenylsulfonyl, 2-methylphenylsulfonyl, 2-methoxyphenylsulfonyl or 2-chlorophenylsulfonyl.

$R^6$ is for example methoxycarbonyl, ethoxycarbonyl, propoxycarbonyl, isopropoxycarbonyl, butoxycarbonyl, isobutoxycarbonyl, sec-butoxycarbonyl, mono- or dimethylcarbamoyl, mono- or diethylcarbamoyl, mono- or dipropylcarbamoyl, mono- or diisopropylcarbamoyl, mono- or dibutyloarbamoyl or N-methyl-N-ethylcarbamoyl.

Preference is given to naphtholactam derivatives of the formula I where $R^1$ is hydrogen.

Preference is further given to naphtholactam derivatives of the formula I where $R^2$ is hydrogen, Preference is further given to naphtholactam derivatives of the formula I where $R^3$ is hydrogen, $C_2$–$C_4$-alkanoyl, benzoyl, halogen, nitro, $C_1$–$C_6$-alkylthio, phenylthio or together with $R^4$ a radical of the formula

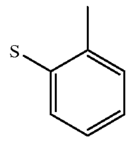

Preference is further given to naphtholactam derivatives of the formula I where $R^5$ is hydrogen or methyl, especially hydrogen.

Preference is further given to naphtholactam derivatives of the formula I where $R^6$ is cyano.

Preference is further given to naphtholactam derivatives of the formula I where $R^7$ is $C_5$–$C_{13}$-alkyl with or without substitution by phenoxy and with or without interruption by from 1 to 3 oxygen atoms in ether function, or is phenylethyl.

Particular preference is given to naphtholactam dyes of the formula I where $R^7$ is $C_6$–$C_{13}$-alkyl, especially $C_7$–$C_{13}$-alkyl, $C_5$–$C_{13}$-alkyl which is interrupted by 1 or 2 oxygen atoms in ether function, or phenylethyl.

Particular preference is further given to naphtholactam derivatives of the formula Ia (Ia)

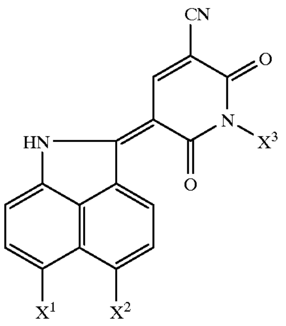

where $X^1$ is hydrogen, $C_2$–$C_4$-alkanoyl, benzoyl, nitro, $C_{1-C6}$-alkylthio or phenylthio, $X^2$ is hydrogen or together with $X^1$ a radical of the formula

6

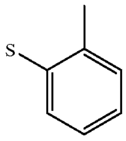

and $X^3$ is $C_5$–$C_{13}$-alkyl with or without substitution by phenoxy and with or without interruption by from 1 to 3 oxygen atoms in ether function, or is phenylethyl.

The naphtholactam derivatives of the formula I according to the present invention can be obtained by conventional methods.

For example, a naphtholactam of the formula IIa or IIb (IIa)

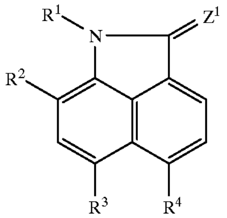

-continued (IIb)

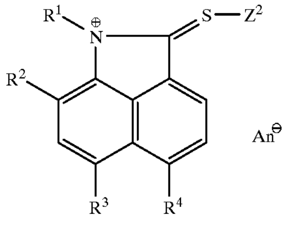

where $Z^1$ is oxygen or sulfur, $Z^2$ is $C_1$–$C_4$-alkyl and An⊖ is the equivalent of an anion (e.g. halide, methosulfate or ethosulfate) and $R^1$, $R^2$, $R^3$ and $R^4$ are each as defined above, can be condensed with a pyridone of the formula III (III)

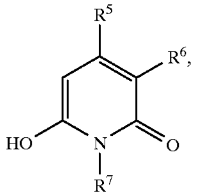

where $R^5$, $R^6$ and $R^7$ are each as defined above.

A condensing agent is required in the case of $Z^1$ oxygen, but not in the case of compounds where $Z^1$ is sulfur or which conform to the formula Ib.

Examples of suitable condensing agents include phosphorus halides, such as phosphorus pentachloride, phosphorus trichloride, phosphorus oxychloride or phosphorus oxybromide. The use of phosphorus oxychloride is preferred.

The reaction can be carried out in a diluent, for example a glycol ether, such as methylglycol, ethylglycol, methyldiglycol or ethyldiglycol, γ-butyrolactone, dichloroethane, chlorobenzene, dichlorobenzene, nitrobenzene or dioxane, or else in an excess of condensing agent, If the reaction of the naphtholactams is carried out without a condensing agent, the abovementioned diluents are likewise also suitable, but in addition there may be mentioned for example pyridine, N,N-dimethylformamide or N-methylpyrrolidone.

The naphtholactam derivatives of the formula I according to the present invention are advantageously useful for dyeing or printing textile materials These exhibit for example fibers or fabrics made of cellulose esters or polyesters but also of polyamides, or blends of polyesters and cellulose fibers. The dyeings or prints obtained have a high fastness to dry heat setting and pleating, a high color strength and a high brilliance and also good in-use/service fastness properties.

To obtain a favorable color build-up, it can be of advantage in some cases to dye with mixtures between the naphtholactam derivatives of the formula I.

The naphtholactam derivatives of the present invention are also advantageously useful for thermal transfer from a transfer to plastic-coated paper by means of an energy source (see e.g. EP-A-416 434).

The Examples which follow illustrate the invention.

EXAMPLE 1

8.2 ml (0.09 mol) of phosphoryl chloride were added dropwise with stirring at 80° C. to a mixture of 150 ml of γ-butyrolactone, 8.2 g (0.03 mol) of 4-benzoylnaphtholactam and 7.3 g (0.037 mol) of 1-(4-oxahexyl)-3-cyano-6-hydroxypyrid-2-one. The reaction mixture was stirred at 120° C. for 6 h and then distilled at 0.5–0.7 mbar and 50–54° C. to remove γ-butyrclactone and phosphorus oxychloride, 70 ml of ethanol were then gradually added dropwise at the same temperature with stirring, and the mixture was cooled down to room temperature and stirred at room temperature for 2 h. The dye was then filtered off, washed with petroleum ether and dried to leave 7.5 g (54%) of the dye of the formula

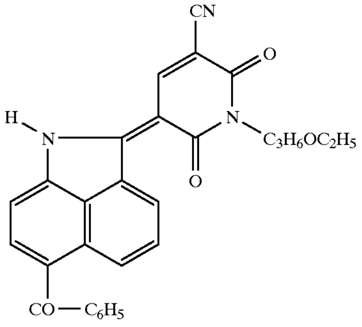

in the form of red crystals.

(mp.: 128–135° C.; $\lambda_{max}$: 278 nm, 548 nm, in $CH_2Cl_2$)

EXAMPLE 2 a) 5 g (0.02 mol) of 4-bromonaphtholactam, 2.3 g (0.022 mol) of styrene, 3.9 g (0.21 mol) of tributylamine, 0.052 g (0.0002 mol) of triphenylphosphine and 0.0022 g (0.00001 mol) of palladium acetate were combined under nitrogen and heated to 150° C. for 4 h with stirring. The mixture was then cooled down to room temperature and dissolved in 1200 ml of acetone with heating, and the catalyst was filtered off. The solution was then slowly concentrated at room temperature, obtaining 4.16 g (77%) of crystals of a yellow product of the formula

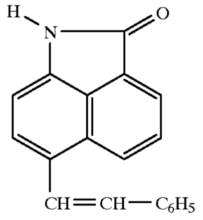

b) 1.48 g of the compound obtained under a) were condensed with 1.47 g of 1-hexyl-3-cyano-6-hydroxypyrid-2-one by the method of Example 2, affording 2.34 g (90%) of the compound of the formula

9

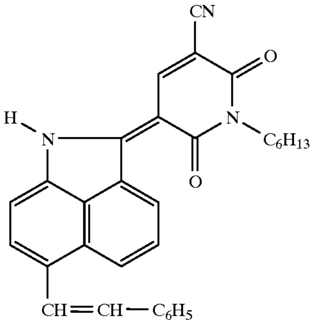

($\lambda_{max}$: 558 nm, in $CH_2Cl_2$)

EXAMPLE 3

8.4 g (0.05 mol) of naphtholactam and 11.6 g (0.05 mol) of 1-heptyl-3-cyano-6-hydroxypyrid-2-one were stirred at 50° C. in 35 ml of 1,2-dichloroethane for 15 min. Thereafter 10 ml of phosphorus oxychloride were added dropwise, and stirring was continued for a further 2 h at 80° C. Thereafter excess phosphorus oxychloride was discharged at room temperature, which also brought down the product. The mixture was subsequently stirred overnight at room temperature and filtered with suction, and the filter residue was washed with methanol, leaving 8.71 g (45.2%) of a product of the formula

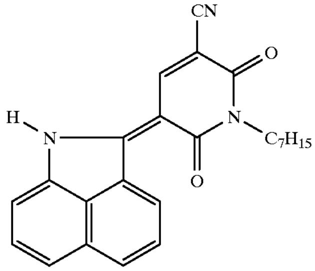

(mp.: 212° C.;$\lambda_{max}$: 507 nm, 544 nm, in $CH_2Cl_2$)

The same method can be used to obtain the naphtholactam derivatives listed below:

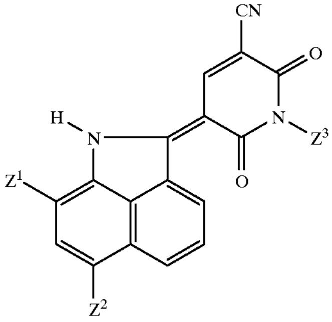

| Ex. No. | $Z^1$ | $Z^2$ | $Z^3$ | mp. [° C.] | $\lambda_{max}$ ($CH_2Cl_2$) [nm] | Hue on polyester |
|---|---|---|---|---|---|---|
| 3 | H | $COC_6H_5$ | $C_6H_{13}$ | >230 | 510, 550 | red |
| 4 | H | $SC_6H_5$ | $C_6H_{13}$ | 199–205 | 518 556 | violet |
| 5 | H | $COC_3H_7$ | $C_6H_{13}$ | 158–166 | 510, 548 | red |
| 6 | H | $COC_6H_5$ | $CH_2(C_2H_5)C_4H_9$ | 102–156 | 510 550 | red |
| 7 | H | $COC_3H_7$ | $C_3H_6OC_2H_5$ | 120–145 | 360, 548 | red |
| 8 | H | $NO_2$ | $CH_2(C_2H_5)C_4H_9$ | >230 | 556 | violet |
| 9 | H | $COC_3H_7$ | $CH_2(C_2H_5)C_4H_9$ | 168–177 | 510, 548 | red |
| 10 | H | $SO_2CH_3$ | $CH_2(C_2H_5)C_4H_9$ | 190–204 | 520, 560 | red |
| 11 | H | $NO_2$ | $C_6H_{13}$ | | 518, 556 | red |
| 12 | H | $SO_2CH_3$ | $C_6H_{13}$ | | 518, 558 | red |
| 13 | H | $C{\equiv}CC(CH_3)_2OH$ | $C_6H_{13}$ | | 570 | violet |
| 14 | H | $CH{=}C(CH_3)COOC_{13}H_{27}$ | $C_6H_{13}$ | | 564 | red |
| 15 | H | H | $(CH_2)_3O(CH_2)_2OC_6H_5$ | 136 | 507, 544 | |
| 16 | H | H | $CH_2(C_2H_5)C_4H_9$ | 181–194 | 506, 544 | |
| 17 | H | H | $C_6H_{13}$ | 218 | 507, 544 | |

-continued

| Ex. No. | $Z^1$ | $Z^2$ | $Z^3$ | mp. [° C.] | $\lambda_{max}$ ($CH_2Cl_2$) [nm] | Hue on polyester |
|---|---|---|---|---|---|---|
| 18 | H | H | $CH_2C(CH_3)_3$ | | 523, 557 | red |
| 19 | H | H | $C_2H_4(C_2H_5)C_4H_9$ | | | red |
| 20 | 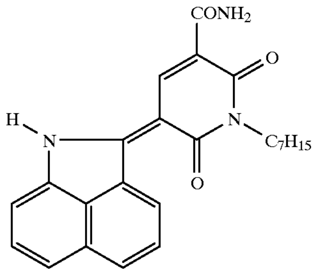 (mp.: 250° C.; $\lambda_{max}$: 515 nm, in N,N-Dimethylformamide) | | | | | |
| 21 | 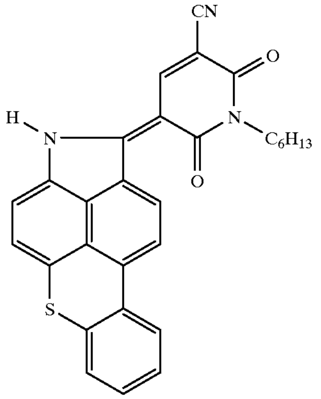 (mp.: 618 nm, 672 nm, in $CH_2Cl_2$) | | | | | |

We claim:

1. An naphtholactam derivative of the formula I (I)

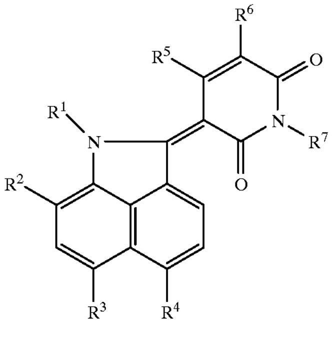

where $R^1$ is hydrogen, substituted or unsubstituted $C_1$–$C_6$-alkyl, $C_5$–$C_7$-cycloalkyl or substituted or unsubstituted phenyl, $R^2$ and $R^3$ are independently of each other hydrogen, $C_1$–$C_8$-alkanoyl, substituted or unsubstituted benzoyl, substituted or unsubstituted $C_2$–$C_4$-alkyl, substituted or unsubstituted $C_2$–$C_4$-alkenyl, substituted or unsubstituted $C_2$–$C_4$-alkynyl, nitro, sulfamoyl, hydroxyl, mercapto, $C_1$–$C_6$-alkoxy, substituted or unsubstituted phenoxy, $C_1$–$C_6$-alkylthio, substituted or unsubstituted phenylthio, $C_1$–$C_6$-alkylsulfonyl or substituted or unsubstituted phenylsulfonyl, with the proviso that one of $R^2$ and $R^3$ is other than hydrogen, $R^4$ is hydrogen or together with $R^3$ a radical of the formula

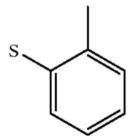

$R^5$ is hydrogen, $R^6$ is cyano, carbamoyl, mono- or di($C_1$–$C_4$-alkyl) carbamoyl, carboxyl or $C_1$–$C_4$-alkoxycarbonyl, and $R^7$ is substituted or unsubstituted $C_5$–$C_{13}$-alkyl with or without interruption by from 1 to 3 oxygen atoms in ether function, by from 1 to 3 sulfur atoms or by from 1 to 3 imino or $C_1$–$C_4$-alkylimino groups, or is benzoyl.

2. A naphtholactam derivative as claimed in claim 1 wherein $R^1$ is hydrogen.

3. A naphtholactam derivative as claimed in claim 1 wherein $R^2$ is hydrogen.

4. A naphtholactam derivative as claimed in claim 1 wherein $R^3$ is hydrogen $C_2$–$C_4$-alkanoyl, benzoyl, nitro, $C_1$–$C_6$-alkylthio, phenylthio or together with $R^4$ a radical of the formula

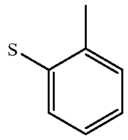

5. A naphtholactam derivative as claimed in claim 1 wherein $R^5$ is hydrogen or methyl.

6. A naphtholactam derivative as claimed in claim 1 wherein $R^6$ is cyano.

7. A naphtholactam derivative as claimed in claim 1 wherein R7 is $C_5$–$C_{13}$-alkyl with or without substitution by phenoxy and with or without interruption by from 1 to 3 oxygen atoms in ether function, or is phenylethyl.

8. A naphtholactam derivative as claimed in claim 1 wherein $R^7$ is $C_6$–$C_{13}$-alkyl, $C_5$–$C_{13}$-alkyl which is interrupted by 1 or 2 oxygen atoms in ether function, or phenylethyl.

9. A naphtholactam derivative as claimed in claim 1 of the formula Ia (Ia)

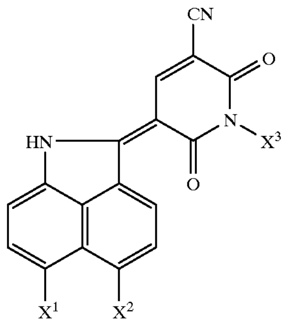

where $X^1$ is, $C_2$–$C_4$-alkanoyl, benzoyl, nitro, $C_1$–$C_6$-alkylthio or phenylthio, $X^2$ is hydrogen or together with $X^1$ a radical of the formula

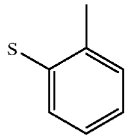 and $X^3$ is $C_5$–$C_{13}$-alkyl with or without substitution by phenoxy and with or without interruption by from 1 to 3 oxygen atoms in ether function, or is phenylethyl.

10. A method comprising dyeing or printing textile materials with a naphtholactam derivative of claim 1.

11. The naphtholactam derivatives of Claim 1, having the following formula:

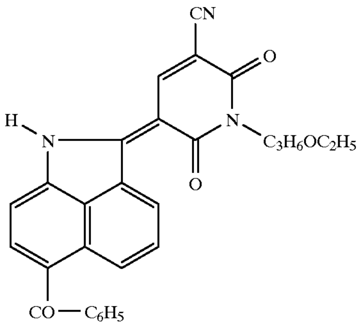

* * * * *